US010159195B2

(12) United States Patent
Green (10) Patent No.: US 10,159,195 B2
(45) Date of Patent: Dec. 25, 2018

(54) SYSTEMS AND METHODS FOR PLANT STRESS MITIGATION

(71) Applicant: AgroFresh Inc., Collegeville, PA (US)

(72) Inventor: Alan Ward Green, Des Moines, IA (US)

(73) Assignee: AGROFRESH INC., Philadelphia, PA (US)

(*) Notice: Subject to any disclaimer, the term of this patent is extended or adjusted under 35 U.S.C. 154(b) by 521 days.

(21) Appl. No.: 14/765,177

(22) PCT Filed: Feb. 6, 2014

(86) PCT No.: PCT/US2014/015092
§ 371 (c)(1),
(2) Date: Jul. 31, 2015

(87) PCT Pub. No.: WO2014/124128
PCT Pub. Date: Aug. 14, 2014

(65) Prior Publication Data
US 2015/0359183 A1 Dec. 17, 2015

Related U.S. Application Data

(60) Provisional application No. 61/762,536, filed on Feb. 8, 2013.

(51) Int. Cl.
*A01G 7/06* (2006.01)
*A01N 25/00* (2006.01)
(Continued)

(52) U.S. Cl.
CPC .............. *A01G 7/06* (2013.01); *A01N 25/00* (2013.01); *A01N 27/00* (2013.01); *C12Q 1/6895* (2013.01);
(Continued)

(58) Field of Classification Search
None
See application file for complete search history.

(56) References Cited

U.S. PATENT DOCUMENTS

| 5,539,637 A | 7/1996 | Upchurch et al. |
| 5,764,819 A | 9/1998 | Orr et al. |
| 6,567,537 B1 | 5/2003 | Anderson |

FOREIGN PATENT DOCUMENTS

| WO | WO 02/079376 A2 | 10/2002 |
| WO | WO 2010/117944 A1 | 10/2010 |
| WO | WO 2011/153445 A1 | 12/2011 |

OTHER PUBLICATIONS

Djanaguiraman M et al: Ethylene perception inhibitor 1-MCP decreases oxidative damage of leaves through enhanced antioxidant defense mechanisms in soybean plants grown under temperature stress, Environmental and Experimental Botany, Elsevier, Amsterdam, NL, vol. 71, No. 2, Dec. 4, 2010.

(Continued)

*Primary Examiner* — Larry D Riggs, II
(74) *Attorney, Agent, or Firm* — Barnes & Thornburg LLP (57) ABSTRACT

Provided are systems and methods for plant stress mitigation. The systems provided comprises three key components to perform a self-standardized algorithm for identifying/measuring significant stress conditions within a short time window (for example 1 to 3 days). After identification of a significant stress condition, plants under stress can be treated with a composition comprising an ethylene synthesis or perception inhibitor, for example 1-methylcyclopropene (1-MCP). Also provided are methods for identifying plant genes in response to stress using the system disclosed herein.

29 Claims, 2 Drawing Sheets

(51) Int. Cl.
- *A01N 27/00* (2006.01)
- *C12Q 1/6895* (2018.01)
- *G01N 33/00* (2006.01)
- *G06F 19/22* (2011.01)

(52) U.S. Cl.
CPC ......... *G01N 33/0098* (2013.01); *G06F 19/22* (2013.01); *C12Q 2600/13* (2013.01); *C12Q 2600/158* (2013.01)

(56) References Cited

OTHER PUBLICATIONS

International Search Report dated Apr. 24, 2014.

SYSTEMS AND METHODS FOR PLANT STRESS MITIGATION

BACKGROUND OF THE INVENTION

There are significant agricultural research efforts to identify and quantify drought stress in crops in order to optimally time irrigation applications or other mitigating measures. Systems commonly used are measures of soil water content, estimated evapotranspiration, and FAO 56 water balance calculation. Many systems tried to date are either too late in detecting the stress, inconsistent across locations, or both. Growers need reliable ways of detecting small changes in stress in order to provide sufficient time to react with stress management measures (irrigate, spray). Researchers also need objective and consistent tool to characterize stress on a daily basis across locations and time.

Thus, there remains a need for improved systems and methods for plant stress mitigation.

SUMMARY OF THE INVENTION

Provided are systems and methods for plant stress mitigation. The systems provided comprises three key components to perform a self-standardized algorithm for identifying/measuring significant stress conditions within a short time window (for example 1 to 3 days). After identification of a significant stress condition, plants under stress can be treated with a composition comprising an ethylene synthesis or perception inhibitor, for example 1-methylcyclopropene (1-MCP). Also provided are methods for identifying plant genes in response to stress using the system disclosed herein.

In one aspect, provided is a computer-implemented system for plant stress identification or mitigation. The system comprises:
  (a) a baseline module for providing a standardized baseline for an unstressed crop based a mid-term historical average;
  (b) a detection module for detecting a short term change to quantify amount of change in stress; and
  (c) a comparison module for comparing changes between short term slope of Tc-Ta and long term slope of Tc-Ta to indicate a significant change in stress conditions, wherein Tc refers to temperature of canopy and Ta refers to ambient temperature.

In another embodiment the mid-term is from 5 days to 14 days. In another embodiment, the short term is from 1 day to 3 days. In another embodiment, the long term is from 14 days to 30 days.

In another aspect, provided is a method for plant stress mitigation. The method comprises:
  (a) identifying a significant change in stress conditions using the system provided herein; and
  (b) contacting the plant with a composition comprising an ethylene synthesis or perception inhibitor.

In one embodiment, the method provided further comprises treating the plant with another stress mitigation measure. In a further embodiment, the another stress mitigation measure comprises applying water to the plant. In another embodiment, the ethylene synthesis or perception inhibitor comprises a cyclopropene compound, a strobilurene, or an aminovynilglycine. In another embodiment, the ethylene synthesis or perception inhibitor comprises a cyclopropene compound, strobiurene fungicide, cytokinen (growth regulator) compounds, Potassium (KCl) or an aminovynilglycine. In another embodiment, the ethylene synthesis or perception inhibitor is selected from a group consisting of a cyclopropene compound, strobiurene fungicide, cytokinen (growth regulator) compounds, Potassium (KCl), an aminovynilglycine, or combinations thereof. In another embodiment, the cyclopropene compound is part of a cyclopropene molecular complex. In another embodiment, the cyclopropene molecular complex comprises an inclusion complex of a molecular encapsulating agent and a cyclopropene compound.

In another embodiment, the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In another embodiment, the cyclopropene compound is of the formula:

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

In a further embodiment, the cyclopropene comprises 1-methylcyclopropene (1-MCP). In another embodiment, the molecular encapsulating agent is selected from the group consisting of alpha-cyclodextrin, beta-cyclodextrin, gamma-cyclodextrin, and combinations thereof. In another embodiment, the molecular encapsulating agent comprises alpha-cyclodextrin.

In another aspect, provided is a method for identifying plant genes in response to stress. The method comprises:
  (a) measuring a first expression profile for a control unstressed plant;
  (b) detecting a significant change in stress conditions using the system provided herein;
  (c) measuring a second expression profile for a stressed plant under stress conditions of step (b); and
  (d) comparing the first expression profile and the second expression profile to identify alteration in expression, thereby identifying plant genes in response to the stress conditions.

In one embodiment, the plant genes comprise wild-type genes. In another embodiment, the plant genes comprise transgenes. In another embodiment, the alteration in expression is expressed as a mean or average, a numerical mean or range of numerical means, a numerical pattern, a graphical pattern, or an expression profile. In another embodiment, the alteration in expression is selected from the group consisting of:
  (a) an up-regulation of a gene or gene product;
  (b) a down-regulation of a gene or gene product;
  (c) a change in identity or expression of a gene or gene product; and (d) combinations thereof.

In another embodiment, contacting a composition comprising an ethylene synthesis or perception inhibitor reverses at least in part of the alteration in expression. In another embodiment, the ethylene synthesis or perception inhibitor comprises a cyclopropene compound, a strobilurene, or an aminovynilglycine. In another embodiment, the ethylene synthesis or perception inhibitor comprises a cyclopropene compound, strobiurene fungicide, cytokinen (growth regulator) compounds, Potassium (KCl) or an aminovynilglycine. In another embodiment, the ethylene synthesis or perception inhibitor is selected from a group consisting of a cyclopropene compound, strobiurene fungicide, cytokinen (growth regulator) compounds, Potassium (KCl), an aminovynilglycine, or combinations thereof. In another embodiment, the cyclopropene compound is part of a cyclopropene molecular complex. In another embodiment, the cyclopropene molecular complex comprises an inclusion complex of a molecular encapsulating agent and a cyclopropene compound.

In another embodiment, the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In another embodiment, the cyclopropene compound is of the formula:

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

In a further embodiment, the cyclopropene comprises 1-methylcyclopropene (1-MCP). In another embodiment, the molecular encapsulating agent is selected from the group consisting of alpha-cyclodextrin, beta-cyclodextrin, gamma-cyclodextrin, and combinations thereof. In another embodiment, the molecular encapsulating agent comprises alpha-cyclodextrin.

DETAILED DESCRIPTION OF THE INVENTION

It is known that a crop can be considered "under stress" when the temperature of the crop canopy approaches or exceeds a threshold temperature. However, the critical threshold temperature varies and is dependent on the location, its conditions (mainly temperature, solar radiation, humidity and wind), and the crop species. There are no standard threshold temperatures that are universally applicable to diverse environments or different crop species.

Past experiments have shown that (1) changes in canopy temperature tend to occur long before visible signs of stress develop; (2) infrared thermometry (IRT) can detect very small changes in canopy temperature; (3) changes in canopy temperatures as detected by IRT's are reflective of a compilation of the soil-air-plant-water interaction. No previously disclosed single instrument is able to integrate all factors. While it is known that these instruments can be used this way, what is not known is how to interpret that data using an algorithm to demonstrate early stages of crop stress.

The overall problem is one of unpredictable and significant yield losses associated with the inability to accurately and reliably detect and objectively quantify stress. If one takes stress relief measures when there really is not stress they have wasted effort and money and if one reacts to slowly to the development of stress, they have lost valuable time and the benefit of stress mitigation efforts.

The systems and methods provided have at least one of the following advantages: (1) using a unique and innovative universally applicable algorithm involving data from infrared thermometry (IRT) to monitor crop canopy temperatures for the early detection and quantification of plant stress; (2) mitigating same plant stress through use of 1-MCP or other measures; (3) utilizing the algorithm for the evaluation/screening of various stress genes for crop stress mitigation, and (4) utilizing the algorithm to evaluate crop genetic lines/hybrids for drought stress improvement.

In the first aspect, the subject invention provides a self standardizing algorithm that can be universally applied to detect changes in plant stress before it is visible to the naked eye and objectively quantify that stress over time and space. This improved approach is comprised of three components: (1) The mid-term historical average (5-14 days) as standardized baseline for an unstressed crop; (2) The short term recent (3 day) change to quantify the amount change/increase in stress; and (3) The change in short term recent (3 day) slope of the Tc—Ta versus long term (14 day) slope of Tc—Ta is used to indicate a significant change in conditions.

In the second aspect, the subject invention provides the use of identification of developing stress above as an indicator appropriate timing to apply a chemical stress mitigation agent such as 1-MCP or take some other management action in order to minimize negative impacts on yield.

In the third aspect, the subject invention provides an algorithm developed and evaluate which genes are switched on or off at the earliest stages of stress so that these genes can be targeted for improvement In the fourth aspect, the subject invention provides the use of the algorithm to evaluate crop lines for genetic improvement.

The practice of the present invention involves the use of one or more cyclopropene compound. As used herein, a cyclopropene compound is any compound with the formula where each $R^1$, $R^2$, $R^3$ and $R^4$ is independently selected from the group consisting of H and a chemical group of the formula:

$$-(L)_n-Z$$

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl, butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In one embodiment, one or more of $R^1$, $R^2$, $R^3$, and $R^4$ is hydrogen or $(C_1-C_{10})$ alkyl. In another embodiment, each of $R^1$, $R^2$, $R^3$, and $R^4$ is hydrogen or $(C_1-C_8)$ alkyl. In another embodiment, each of $R^1$, $R^2$, $R^3$, and $R^4$ is hydrogen or $(C_1-C_4)$ alkyl. In another embodiment, each of $R^1$, $R^2$, $R^3$, and $R^4$ is hydrogen or methyl. In another embodiment, $R^1$ is $(C_1-C_4)$ alkyl and each of $R^2$, $R^3$, and $R^4$ is hydrogen. In another embodiment, $R^1$ is methyl and each of $R^2$, $R^3$, and $R^4$ is hydrogen, and the cyclopropene compound is known herein as 1-methylcyclopropene or "1-MCP."

In one embodiment, a cyclopropene compound can be used that has boiling point at one atmosphere pressure of 50° C. or lower; 25° C. or lower; or 15° C. or lower. In another embodiment, a cyclopropene compound can be used that has boiling point at one atmosphere pressure of −100° C. or higher; −50° C. or higher; −25° C. or higher; or 0° C. or higher.

The composition of the present invention includes at least one molecular encapsulating agent. In preferred embodiments, at least one molecular encapsulating agent encapsulates one or more cyclopropene compound or a portion of one or more cyclopropene compound. A complex that contains a cyclopropene compound molecule or a portion of a cyclopropene compound molecule encapsulated in a molecule of a molecular encapsulating agent is known herein as a "cyclopropene compound complex" or "cyclopropene molecular complex."

In one embodiment, at least one cyclopropene compound complex is present that is an inclusion complex. In a further embodiment for such an inclusion complex, the molecular encapsulating agent forms a cavity, and the cyclopropene compound or a portion of the cyclopropene compound is located within that cavity.

In another embodiment for such inclusion complexes, the interior of the cavity of the molecular encapsulating agent is substantially apolar or hydrophobic or both, and the cyclopropene compound (or the portion of the cyclopropene compound located within that cavity) is also substantially apolar or hydrophobic or both. While the present invention is not limited to any particular theory or mechanism, it is contemplated that, in such apolar cyclopropene compound complexes, van der Waals forces, or hydrophobic interactions, or both, cause the cyclopropene compound molecule or portion thereof to remain within the cavity of the molecular encapsulating agent.

The amount of molecular encapsulating agent can usefully be characterized by the ratio of moles of molecular encapsulating agent to moles of cyclopropene compound. In one embodiment, the ratio of moles of molecular encapsulating agent to moles of cyclopropene compound can be 0.1 or larger; 0.2 or larger; 0.5 or larger; or 0.9 or larger. In another embodiment, the ratio of moles of molecular encapsulating agent to moles of cyclopropene compound can be 10 or lower; 5 or lower; 2 or lower; or 1.5 or lower.

Suitable molecular encapsulating agents include, for example, organic and inorganic molecular encapsulating agents. Suitable organic molecular encapsulating agents, which include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In one embodiment, the encapsulating agent is alpha-cyclodextrin, beta-cyclodextrin, gamma-cyclodextrin, or combinations thereof. In a further embodiment, alpha-cyclodextrin is used.

Provided is a method of making the powder composition of the present invention. The method includes the step of making a powder (herein called the "complex powder" or "HAIP" for High-loaded Active Ingredient Particles) that contains cyclopropene compound complex. Usually, each particle of the complex powder contains many molecules of molecular encapsulating agent in which a molecule of a cyclopropene compound is encapsulated. The complex powder may also contain one or more adjuvants, including, for example, one or more mono- or di-saccharide compound, one or more metal complexing agent, or combinations thereof.

In one embodiment, complex powders may have median particle diameter of 10 micrometers or less; 7 micrometers or less; or 5 micrometers or less. In another embodiment, complex powders may have median particle diameter of 0.1 micrometer or more; or 0.3 micrometer or more. Median particle diameter may be measured by light diffraction using a commercial instrument such as those manufactured, for example, by Horiba Co. or Malvern Instruments.

The composition used in the present invention may comprise a formation of an aqueous slurry. An aqueous slurry can be formed when a composition is mixed with an aqueous medium. To form such a slurry, the aqueous medium may be mixed directly a solid composition. The amount of composition provided in the slurry may be characterized by the concentration of cyclopropene compound in the slurry. In one embodiment, suitable slurries may have cyclopropene compound concentration, in units of milligrams of cyclopropene compound per liter of slurry, of 2 or higher; 5 or higher; or 10 or higher. In another embodiment, suitable slurries may have cyclopropene compound concentration, in units of milligrams of cyclopropene compound per liter of slurry, of 1000 or lower; 500 or lower; or 200 or lower.

The amount of water in the aqueous medium used in the slurry may be, by weight based on the weight of aqueous medium, 80% or more; 90% or more; or 95% or more.

The slurry may optionally contain one or more adjuvants, for example, one or more metal complexing agent, one or more surfactant, one or more oil, one or more alcohol, or mixtures thereof. Examples of metal-complexing agents, if used, include chelating agents. Examples of surfactants, if used, include anionic surfactants, non-ionic surfactants, and silicone surfactants. Examples of alcohols, if used, include alkyl alcohols with 4 or fewer carbon atoms. Oils are compounds that are liquid at 25° C., are not water, are not surfactants, and are not alcohols. Examples of oils, if used, include hydrocarbon oils and silicone oils.

Plants or plant parts may be treated in the practice of the present invention. One example is treatment of whole plants; another example is treatment of whole plants while they are planted in soil, prior to the harvesting of useful plant parts.

Any plants that provide useful plant parts may be treated in the practice of the present invention. Examples include plants that provide fruits, vegetables, and grains.

As used herein, the phrase "plant" includes dicotyledons plants and monocotyledons plants. Examples of dicotyledons plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale. Examples of fruit include papaya, banana, pineapple, oranges, grapes, grapefruit, watermelon, melon, apples, peaches, pears, kiwifruit, mango, nectarines, guava, persimmon, avocado, lemon, fig, and berries.

In some embodiments, the methods of the subject invention may comprise a method for use in managing the irrigation of plants comprising:
(a) measuring the canopy temperature of a target plant at a regular interval of time, Ti, using an infrared thermometer;
(b) measuring the atmospheric humidity in the vicinity of said plant;
(c) comparing said canopy temperature with a threshold canopy temperature, said threshold canopy temperature for said plant being approximately that canopy temperature which is effective for optimal plant metabolism, and determining if said humidity is restrictive to plant cooling;
  (1) returning to said step (a) if either: (i) the measured canopy temperature is less than or equal to said threshold canopy temperature, or (ii) said humidity is restrictive to plant cooling;
  (2) adding an increment of time equal to Ti to a time register to provide an accumulated time if both the measured canopy temperature is greater than said threshold canopy temperature, and said humidity is not restrictive to plant cooling;
(d) comparing the accumulated time in said time register to a time threshold, wherein said time threshold is determined as about the mean of the length of time per day that the canopy temperature for said plant in a well-watered and non-stressed condition exceeded said threshold canopy temperature;
  (1) if said accumulated value is greater than or approximately equal to said time threshold, then generating and displaying an irrigation signal, or automatically initiating irrigation, or both;
  (2) returning to said step (a), if said accumulated value is not greater than nor approximately equal to said time threshold.

In some embodiments, the systems of the subject invention may comprise an apparatus for use in managing the irrigation of plants comprising:
(a) an infrared thermometer effective for measuring plant canopy temperature;

(b) a sensing means effective for measuring atmospheric humidity;
(c) a microprocessor effective for comparing the measured canopy temperature to a setpoint temperature, and for comparing the measured humidity to a limiting humidity value; and
(d) a time register operatively connected to said microprocessor effective for accumulating increments of time in response to said microprocessor,
wherein said microprocessor is also effective for comparing the accumulated time in said time register to a setpoint time.

Additional methods and apparatus are disclosed in U.S. Pat. No. 5,539,637, the content of which is incorporated by reference in its entirety.

In some embodiments, the systems of the subject invention may comprise a plant stress prediction system comprising:
(a) a plurality of digital cameras for taking images of a stand of vegetation at different wavelengths, a first of said cameras taking images at wavelengths associated with the absorption spectrum of chlorophyll, a second of said cameras taking images at wavelengths associated with biomass reflectance;
(b) means for computing an Algorithm Image for said stand of vegetation; and
(c) means for displaying said computed Algorithm Image,
wherein said Algorithm Image is produced from digital matrix data obtained from two spectral bandpasses of less than or equal to 25 nm where a first of said two spectral bandpasses includes 680 nm and a second of said two spectral bandpasses includes 770 nm, and where the digital matrix data for the first of said two spectral bandpasses is mapped to a first color forming device and a red/far red data product obtained from the formula ((680 nm/770 nm)+128) is mapped to a second color forming device where said first and second color forming devices form different colors.

In some embodiments, the methods of the subject invention may comprise a method for predicting plant stress or crop yield, said method comprising the steps of:
(a) gathering a plurality of digital images using a photographic system comprised of a plurality of digital cameras equipped with narrow bandpass filters set to detect wavelengths of light corresponding to specific pigment and biomass response regions for vegetation;
(b) transforming said digital images to an "Algorithm Image" representing a chlorophyll content for a stand of vegetation; and
(c) interpreting said Algorithm Image information to predict plant stress or crop yield, wherein said step of transforming said digital images into an "Algorithm Image" further comprises the steps of:
   (1) calculating a ratio of a first digital image of a chlorophyll absorption wavelength and a second digital image of a near infrared plant tissue reflectance wavelength;
   (2) normalizing said ratio to produce a Red/Far Red Data Product; and
   (3) combining said first digital image of a chlorophyll absorption wavelength with said Red/Far Red Data Product, to produce said Algorithm Image, wherein said combination is created by mapping said first digital image and said Red/Far Red Data Product to different color forming devices.

Additional methods and apparatus are disclosed in U.S. Pat. No. 6,567,537, the content of which is incorporated by reference in its entirety.

The present invention is further described in the following examples, which are offered by way of illustration and are not intended to limit the invention in any manner.

EXAMPLES

Example 1

The data used in this Example are generated from field trials conducted in different locations. In each graph, the historic way of detecting stress ex-post is indicated by the Drought Stress line. Two examples of auto-standardized algorithms are depicted as stdized (standardized, where instances >1 indicate developing stress) and stress stdized (stress standardized, where instances >0 indicate developing stress).

Figure 1:
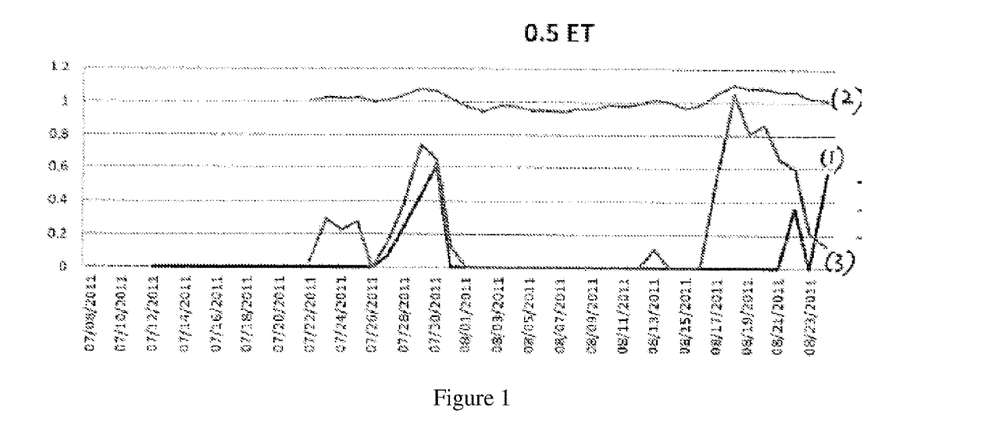
FIG. 1 shows a representative study in which irrigation is managed at only 50% of the daily use in order to impose drought stress. Line (1) shows data from drought stress—0.5ET; line (2) shows data from standardized (Tc3-Ta14)/Ta14; and line (3) shows data from stress standardized (Tc3-Ta14)/Ta14.

FIG. 1 shows representative data from a corn trial conducted in Powell, Wyo. in which irrigation is managed at only 50% of the daily use in order to impose drought stress. The stdized (standardized) line (2) is on the top, and stress stdized (standardized) line (3) is in the middle, where the Drought Stress line (1) is at the bottom of FIG. 1.

Figure 2:
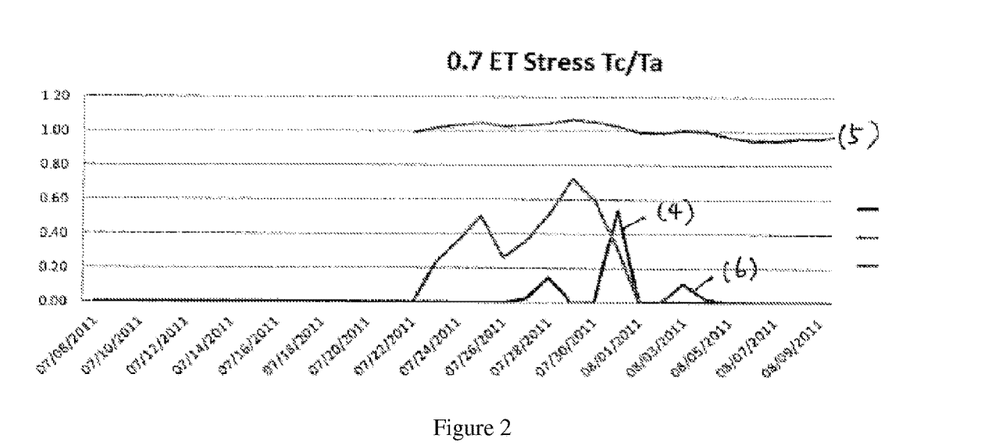
FIG. 2 shows a representative study in which irrigation is managed at 75% of daily use so there was less stress. Line (4) shows data from drought stress—0.7ET; line (5) shows data from standardized (Tc3-Ta14)/Ta14; and line (6) shows data from stress standardized (Tc3-Ta14)/Ta14.

FIG. 2 shows representative data from the same corn trial in Powell, Wyo., but irrigation is managed at 75% of daily use so there is less stress. The stdized (standardized) line (5) is on the top, and stress stdized (standardized) line (6) is in the middle, where the Drought Stress line (4) is at the bottom of FIG. 2.

Figure 3:
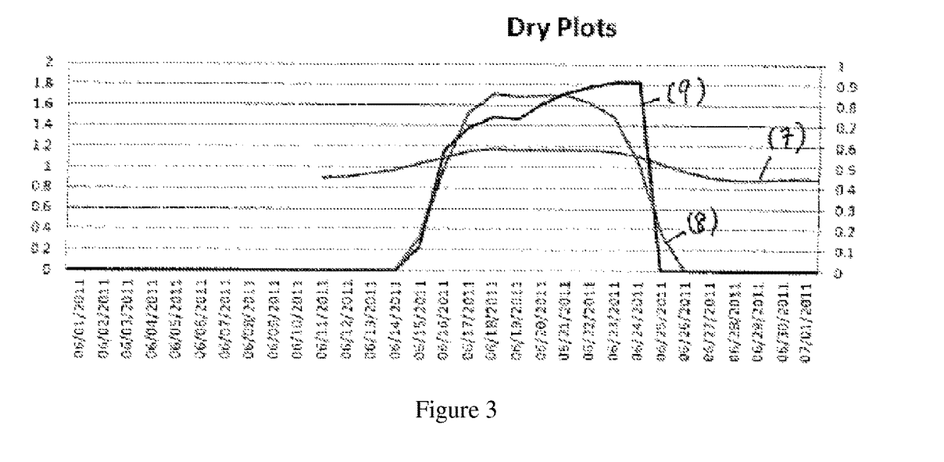
FIG. 3 shows a representative study in which irrigation is completely withheld for about 10 days (normally irrigation are required every 3-5 days to maintain optimal crop growth. Line (7) shows data from standardized (Tc3-Ta14)/Ta14; line (8) shows data from stress standardized (Tc3-Ta14)/Ta14; and line (9) shows data from DSSAT drought.

FIG. 3 shows representative data from another corn trial conducted in Maricopa, Ariz. Here irrigation is completely withheld for about 10 days (normally irrigation are required every 3-5 days to maintain optimal crop growth. The stdized (standardized) line (7); stress stdized (standardized) line (8); and the Drought Stress line (9) are closely to one another as shown in FIG. 3.

In this Example, due to the rapid development of stress after irrigation (3 days), the auto-standardized algorithms do not appear to detect stress ahead of the DSSAT simulation.

Example 2

Location—Ferre 1, Argentina: stress is significantly increased on December 13$^{th}$ and continues until December 18$^{th}$. An application of Invinsa (a liquid formulation comprising 1-MCP) is made on December 13$^{th}$.

Ex-post crop simulation indicates a significant decrease in extractable soil water content but does not estimate an increase in drought stress until beginning on or around December 18$^{th}$.

The application of Invinsa (a liquid formulation comprising 1-MCP) on December 13$^{th}$ results in a statistically significant increase in yield of 1080 kg/ha.

I claim:
1. A method for mitigating drought stress in plants, the method comprising:
   (a) generating field trial data for one or more plants subject to drought stress conditions;
   (b) measuring the temperature of the canopy (Tc) and the ambient temperature (Ta) of the field trial location using infrared thermometry;
   (c) identifying a change in drought stress conditions in the one or more plants using a computer system algorithm for plant stress mitigation, comprising:

(i) a baseline module for providing a standardized baseline for an unstressed crop based on a mid-term historical average, wherein the mid-term historical average is from 5 days to 14 days;

(ii) a detection module for detecting a short term change in drought stress in order to quantify the amount of change in drought stress in the one or more plants subject to drought stress conditions; and (iii) a comparison module for comparing changes between a short term slope of Tc-Ta and a long term slope of Tc-Ta to indicate a change in drought stress conditions, wherein the short term slope is from 1 day to 3 days and the long term slope is from 14 days to 30 days; and (d) contacting the one or more plants subject to the change in drought stress conditions identified in step (c) with a composition comprising an ethylene inhibitor.

2. The method of claim 1, further comprising applying water to the one or more plants.

3. The method of claim 2, wherein applying water to the one or more plants is performed by irrigation.

4. The method of claim 1, wherein the ethylene inhibitor comprises a cyclopropene compound, strobilurin fungicide, cytokinen (growth regulator) compounds, Potassium chloride (KCl), an aminovinylglycine, or combinations thereof.

5. The method of claim 4, wherein the cyclopropene compound is part of a cyclopropene molecular complex.

6. The method of claim 5, wherein the cyclopropene molecular complex comprises an inclusion complex of a molecular encapsulating agent and a cyclopropene compound.

7. The method of claim 4, wherein the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

8. The method of claim 7, wherein R is $C_{1-8}$ alkyl.

9. The method of claim 7, wherein R is methyl.

10. The method of claim 4, wherein the cyclopropene compound is of the formula:

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or naphthyl group; and $R^2$, $R^3$, and $R^4$ are hydrogen.

11. The method of claim 4, wherein the cyclopropene compound comprises 1-methylcyclopropene (1-MCP).

12. The method of claim 6, wherein the molecular encapsulating agent comprises alpha-cyclodextrin, beta-cyclodextrin, gamma-cyclodextrin, or combinations thereof.

13. The method of claim 6, wherein the molecular encapsulating agent comprises alpha-cyclodextrin.

14. A method for identifying plant genes whose expression alters in response to drought stress conditions, the method comprising:

(a) generating field trial data for one or more plants subject to drought stress conditions;

(b) measuring the temperature of the canopy (Tc) and the ambient temperature (Ta) of the field trial location using infrared thermometry;

(c) measuring a first expression profile for a control unstressed plant;

(d) detecting a change in drought stress conditions;

(e) measuring a second expression profile for the one or more plants subject to drought stress conditions of step (a); and (f) comparing the first expression profile and the second expression profile to identify the plant genes whose expression alters in response to the drought stress conditions, wherein the detecting of step (c) is performed using a computer system algorithm for plant stress mitigation, comprising:

(i) a baseline module for providing a standardized baseline for an unstressed crop based on a mid-term historical average, wherein the mid-term historical average is from 5 days to 14 days;

(ii) a detection module for detecting a short term change in drought stress in order to quantify the amount of change in drought stress in the one or more plants subject to drought stress conditions; and (iii) a comparison module for comparing changes between a short term slope of Tc-Ta and a long term slope of Tc-Ta to indicate a change in drought stress conditions, wherein the short term slope is from 1 day to 3 days and the long term slope is from 14 days to 30 days, and (g) contacting the one or more plants subject to drought stress conditions identified in step (a) with a composition comprising an ethylene inhibitor.

15. The method of claim 14, wherein the plant genes comprise wild-type genes.

16. The method of claim 14, wherein the plant genes comprise transgenes.

17. The method of claim 14, wherein the alteration in expression is expressed as a mean or average, a numerical mean or range of numerical means, a numerical pattern, a graphical pattern, or an expression profile.

18. The method of claim 14, wherein the alteration in expression is selected from the group consisting of:

(e) an up-regulation of a gene or gene product;

(f) a down-regulation of a gene or gene product;

(g) a change in identity or expression of a gene or gene product; and (h) combinations thereof.

19. The method of claim 14, wherein the ethylene inhibitor comprises an ethylene synthesis inhibitor or an ethylene perception inhibitor that at least reverses in part alteration in expression.

20. The method of claim 19, wherein the ethylene synthesis or perception inhibitor comprises a cyclopropene compound, strobilurin fungicide, cytokinen (growth regulator) compounds, Potassium chloride (KCl), an aminovinylglycine, or combinations thereof.

21. The method of claim 20, wherein the cyclopropene compound is part of a cyclopropene molecular complex.

22. The method of claim 21, wherein the cyclopropene molecular complex comprise an inclusion complex of a molecular encapsulating agent and a cyclopropene compound.

23. The method of claim 20, wherein the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

24. The method of claim 23, wherein R is $C_{1-8}$ alkyl.

25. The method of claim 23, wherein R is methyl.

26. The method of claim 20, wherein the cyclopropene compound is of the formula:
wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or naphthyl group; and $R^2$, $R^3$, and $R^4$ are hydrogen.

27. The method of claim 20, wherein the cyclopropene compound comprises 1-methylcyclopropene (1-MCP).

28. The method of claim 22, wherein the molecular encapsulating agent comprises alpha-cyclodextrin, beta-cyclodextrin, gamma-cyclodextrin, or combinations thereof.

29. The method of claim 22, wherein the molecular encapsulating agent comprises alpha-cyclodextrin.

* * * * *